(12) United States Patent
Gussmann et al.

(10) Patent No.: US 6,702,833 B1
(45) Date of Patent: Mar. 9, 2004

(54) PROSTHETIC TUBE CONNECTION

(76) Inventors: Andreas Gussmann, Schleusnweg 43, Kleinmachnow D-14532 (DE); Ludwig Metz, deceased, late of Bestensee (DE); by Helga Emma Metz, legal representative, Puschkinstrasse 14, D-15741 Bestensee (DE); by Katharina Metz, legal representative, Puschkinstrasse 14, D-15741 Bestensee (DE); by Dietrich Metz, legal representative, Puschkinstrasse 14, D-15741 Bestensee (DE)

(*) Notice: Subject to any disclaimer, the term of this patent is extended or adjusted under 35 U.S.C. 154(b) by 0 days.

(21) Appl. No.: 09/787,993
(22) PCT Filed: Jun. 17, 1999
(86) PCT No.: PCT/EP99/04192
§ 371 (c)(1),
(2), (4) Date: Jul. 30, 2001
(87) PCT Pub. No.: WO00/16719
PCT Pub. Date: Mar. 30, 2000

(30) Foreign Application Priority Data

Sep. 21, 1998 (DE) ..................... 298 17 771 U

(51) Int. Cl.⁷ ................ A61M 29/00; A61F 2/06
(52) U.S. Cl. ..................... 606/194; 623/1.11
(58) Field of Search ................. 606/153, 151, 606/191, 194; 604/158, 163, 272, 500; 623/1.13, 123.7, 66.1, 1.16, 1.35

(56) References Cited

U.S. PATENT DOCUMENTS

| | | | |
|---|---|---|---|
| 3,648,704 A | * | 3/1972 | Jackson ..................... 604/172 |
| 5,304,220 A | * | 4/1994 | Maginot ..................... 606/159 |
| 5,755,682 A | | 5/1998 | Knudson |
| 5,755,778 A | * | 5/1998 | Kleshinski ................. 606/153 |
| 5,919,225 A | * | 7/1999 | Lau et al. ................... 623/1.2 |
| 5,972,017 A | * | 10/1999 | Berg et al. ................. 606/198 |
| 5,976,178 A | * | 11/1999 | Goldsteen et al. .......... 606/153 |
| 6,019,788 A | * | 2/2000 | Butters et al. ................ 604/8 |

FOREIGN PATENT DOCUMENTS

| | | |
|---|---|---|
| WO | WO 97/12643 | 4/1997 |
| WO | WO 97/43961 | 11/1997 |
| WO | WO 98/19607 | 5/1998 |
| WO | WO 98/19629 | 5/1998 |

* cited by examiner

Primary Examiner—Michael J. Milano
Assistant Examiner—Jessica R Baxter
(74) Attorney, Agent, or Firm—Townsend and Townsend and Crew, LLP

(57) ABSTRACT

The invention relates to a prosthetic tube connection between two arteries or arterial regions inside the human body, comprising a flexible, blood-impermeable prosthetic tube having an appropriate length, whose ends are insertable in the arteries to be connected and connectable to said arteries in a blood-tight manner. According to the invention, a T-shaped tubular metal grid having substantially the diameter of the artery is disposed at least on one end of the tube forming an angle (α) in relation to the longitudinal axis of the corresponding end area of the tube, said grid having a length such that it is insertable into the artery through an orifice made in said artery and extending in both directions of the artery from said orifice. The metal grid is fitted preferably with blood-tight lining and/or jacket, wherein the lining and the metal grid or the jacket in the area of the connection of the tube has a connection orifice in communication with the inner space of the tube and is dimensioned in such a way that the metal grid sealingly rests with the lining and/or jacket in the artery.

18 Claims, 2 Drawing Sheets

PROSTHETIC TUBE CONNECTION

BACKGROUND OF THE INVENTION

The invention relates to a prosthesis tube connection between two arteries, or arterial regions, inside the human body having a flexible, blood-impermeable prosthesis tube of a suitable length whose ends can be introduced into the arteries to be connected and can be connected thereto in a blood-tight manner.

Known prosthesis tube connections substantially consist only of a prosthesis tube made of a primarily impermeable standard prosthesis material. To connect the prosthesis tube to the artery to be connected, e.g. the Aorta abdominales, or the pelvic artery, the artery must be cut open at the connection point and connected to the prosthesis tube consisting of plastic by a manual suture. However, the production of this suture is only possible taking a considerable time and with a considerable risk of error, in particular when using minimally invasive operation techniques. While it has already been attempted to produce the sutures using suitable apparatuses, this is problematic with respect to both the amount of space required and to the operational safety.

A prosthesis tube connection is already known from WO 97/43961 in which a shoulder piece provided with a tube support is fastened to an expandable metal grid provided with an elongate slot, with the prosthesis tube being connectable to the tube support via an adapter consisting of moving parts.

A T-shaped flange connector is k now n from WO 98/19629 which consists of a foldable metal grid and a jacket. The transverse beam of the T-shaped connector is introduced into the artery through an orifice in the folded state and then expanded by a tool. The web of the T-shaped connector then extends from the orifice in the artery so that the base of the T can be connected to the aorta.

FR-27 58 254 discloses a prosthesis tube which is provided with a tubular section at the end and in whose end regions expandable means can be introduced or be arranged from the start.

WO 98/19607 describes the connection of a blood line having an expandable connection segment of plastic by a suture. The connection segment has a non-folded central region at which the suture is provided. Only the end regions, which are excluded from the connection to the blood tube, can be inflated.

SUMMARY OF THE INVENTION

It is an object of the invention to provide a simply designed and simply positionable artificial prosthesis tube connection of the kind initially mentioned with which the implantation of the vessel prosthesis is possible without the time delay caused by the application of the suture, whereby the operation times can be considerably shortened and the risk of a suture breaking and of a bursting open of the connection between the blood vessel and the vessel prosthesis should be banished.

The idea of the invention is therefore to be seen in that, for example, a tubular metal grid known for the widening of arteries, which optionally has an inner lining and/or jacket and which is also known as a stent, is directly connected in a blood-tight manner to a standard prosthesis tube which branches off in T-shaped manner. The folded metal grid having an inner lining and/or jacket and having only a limited length can be introduced into an artery provided with the orifice without problem with the prosthesis tube bent onto the folded metal grid and can then be fixed in place by clamping, in particular by means of self-expansion or balloon expansion, without a suture having to be produced for this purpose. The metal grid having an inner lining and/or jacket must be so long that the two end regions can clearly protrude over the end of the artery incision and ensure the clamping inside the artery. After the operation has been carried out, the incision then grows together again as far as possible, whereby the mounting of the metal grid inside the artery is further improved. Advantageously, special components such as adapters or branches are omitted, whereby a particularly simple design is achieved by only the one end of the prosthesis tube being attached, in particular sutured, directly to an expandable stent. A particular advantage of the direct connection of metal grid and prosthesis tube lies in the fact that the prosthesis tube can be bent onto the folded metal grid, whereby the introduction of the metal grid into the artery through the incision can be carried out without problem.

In addition to the fast and safe application of the prosthesis in an artery, the risk of infection is also reduced by the embodiment in accordance with the invention.

According to another aspect of the invention, an initially folded-up or compressed metal grid can be expanded so far after the introduction into the artery that it is seated securely and fixedly inside the artery.

Other features of the invention improve the flexibility of the tube, or of the jacket, provide an oval orifice which favors the flow of blood from the inside of the metal grid into the tube, and enhance the connection of the tube to the metal grid, or to the inner lining and/or to the jacket.

A particularly stable arrangement is achieved by an embodiment of the invention in which the orifices normally present in the metal grid are also used to lead the blood into the tube without it being necessary to produce an additional orifice in the metal grid.

Another variant of the invention lies in identical lengths of the upstream part, of the downstream part and of the connection point. The length of each of these three elements should be approximately 1.7 cm. The optimum measurements depend on the diameter of the metal grid, the diameter of the metal grid orifice and the diameter of the prosthesis tube.

It is a feature of the invention that the inner lining and/or jacket, including the balloon, of the metal grid can be introduced into the inside of the artery through the orifice therein without problem and can then be expanded to the diameter required for the secure fit inside the artery by inflating the balloon.

According to another aspect of the invention, the metal grid having an inner lining and/or jacket can be brought into the final working position automatically or can be supported by an introduced balloon by pulling the tear line which is guided outwardly through the orifice.

The angle at which the end region of the tube facing the metal grid is arranged relative to the meal grid is preferably in the range between 30° to 60° so that as a result of the oblique connection of the end region of the tube, the folding of the same to the metal grid is favored and so its introduction into the artery simplified.

The invention is described in the following by way of example with reference to the drawing.

BRIEF DESCRIPTION OF THE PREFERRED EMBODIMENTS

Figure 1:
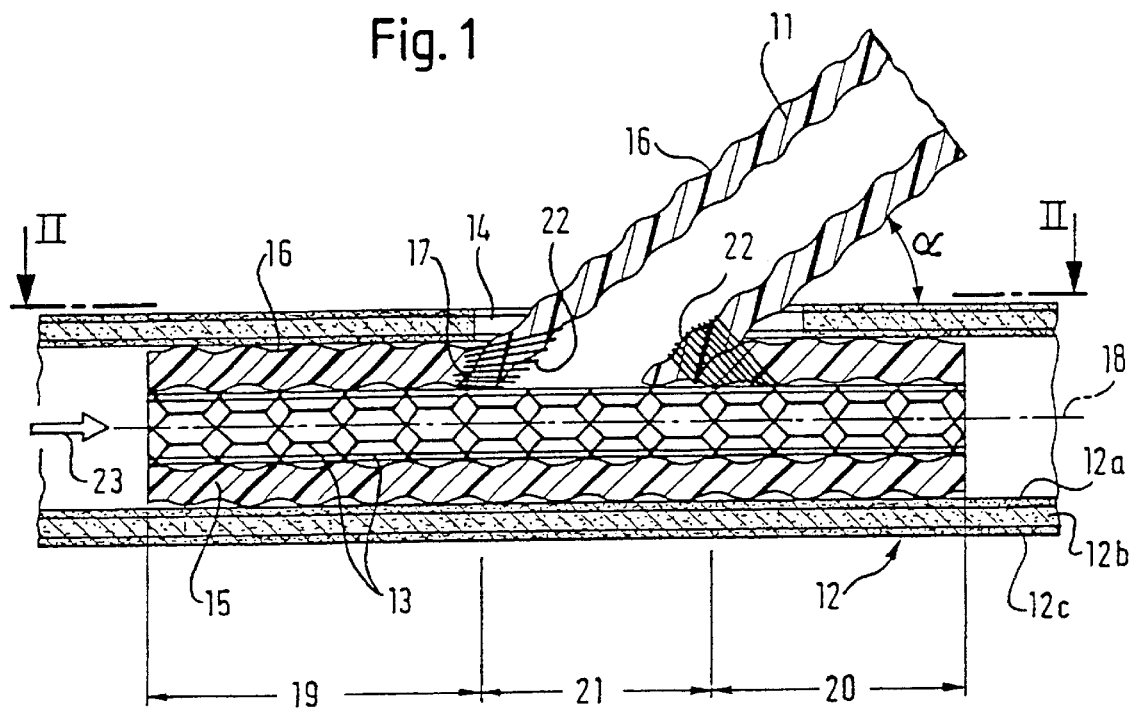
FIG. 1 shows one end region of a prosthesis tube connection in accordance with the invention after the introduction into an artery in a schematic longitudinal sectional view.

In accordance with FIG. 1, a tubular metal grid 13 is provided with a plastic jacket 15. Such jacketed metal grids jacketed stents) are known from aorta surgery in order, for example, to widen the main artery or to reduce the diameter of widened arteries or aorta sections or to seal burst aorta sections.

In accordance with the invention, the jacket 15 is provided at its periphery at a position remote from both ends with an orifice 17 elongated in the direction of the central axis 18 of the metal grid 13, the one end of a prosthesis tube 11 being inserted into said orifice at an angle α, and indeed in such a manner that the material of the tube 11 comes to a stop at the metal grid 13. In this state, the end of the tube 11 is connected in a blood-tight manner to the regions 22 of the jacket 15 surrounding the orifice 17. In this way, a connection point 21 for the prosthesis tube 11 is formed at the metal grid 13 provided with the jacket 15 and starting from this point the metal grid 13 having the jacket 15 extends in both longitudinal directions, with the part 19 extending opposite to the direction 23 of blood flow being somewhat longer than the part 20 of the metal grid 13 having the jacket 15 extending in the direction 23 of blood flow.

Figure 2:
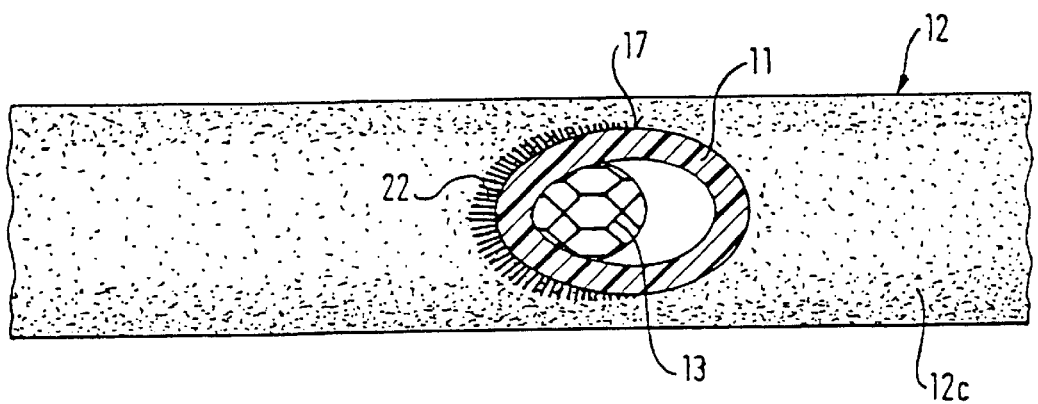
FIG. 2 is a plan view of FIG. 1 and is taken along line II—II in FIG. 1.

As can be seen from FIG. 2, the orifice 17 is formed in an oval manner due to the oblique connection of the end region of the tube 11 to the jacket 15, with the longer axis of the orifice facing in the direction of the central axis 18 of the metal grid 13.

In FIGS. 1 and 2, the described tube connection is shown arranged in an artery 12, which consists of three layers, and indeed of the inner intima 12a, the median media 12b and the outer adventitia 12c. The metal grid 13 having the jacket 15 is introduced into the artery 12 by an oval orifice 14 corresponding to the orifice 17 being provided therein. Subsequently, the longer part 19 is then first pushed through the orifice 14 into the artery 12 in the folded form in accordance with FIG. 3, and indeed so far that subsequently the shorter part 20 can also be introduced into the artery 12 in folded form in the opposite direction. In accordance with FIG. 3, an elongate balloon 24 extending in the direction of its longitudinal axis is introduced into the folded metal grid in a relaxed shape, with a supply tube 25 branching off the side of the balloon 24 in the middle section and being guided through the tube 11 and opening into a valve 26, which has to be opened or closed by hand and which has a connecting cone 27 which can be connected to a compressed air source.

Figure 3:
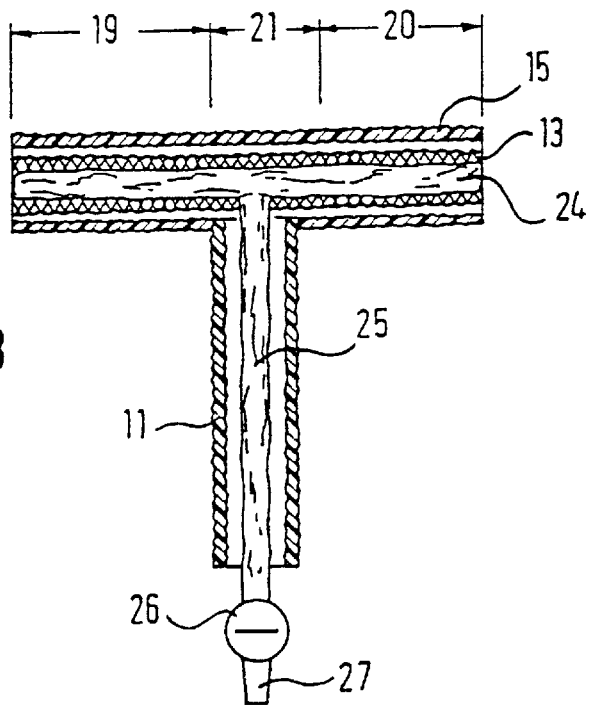
FIG. 3 is a schematic side view of a prosthesis tube connection in accordance with the invention in the folded-up state with the balloon introduced.

In contrast to the representation of FIG. 1, the tube 11 in FIG. 3 branches perpendicularly from the metal grid 13 having a jacket 15.

Figure 4:
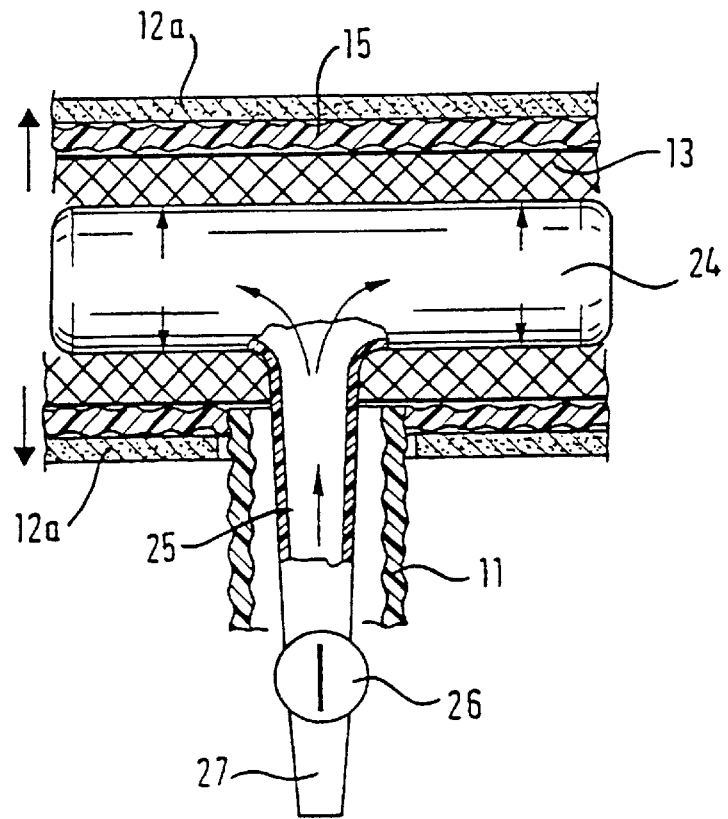
FIG. 4 is a view analog to FIG. 3 after the introduction of the prosthesis tube connection into an artery and the inflation of the balloon.

After a prosthesis tube connection in accordance with the invention according to FIG. 3 has been introduced into an artery 12 with a relaxed balloon 24, the connecting cone 27 is connected to the compressed air source and the valve 26 opened, whereupon, in accordance with FIG. 4, compressed air can flow into the inside of the balloon so that the balloon inflates and an expansion of the metal grid 13 having the jacket 15 takes place for so long until a fixed seat of the metal grid 13 having the jacket 15 is ensured inside the artery 12 without suturing being necessary.

The angle α is selected such that blood flowing in the direction of the arrow 23 cannot flow from the inside of the metal grid 13 into the tube 11 at an angle of 90°, but rather at a much smaller angle than 90°, for example 45°. Part of the blood can, however, flow through the metal grid 13, past the tube 11, into the part of the artery 12 located behind the metal grid.

A metal grid 13 having a jacket 15 can also be arranged in a manner similar to that shown in FIG. 1 at the end of the prosthesis tube 11 not shown in the drawing, in order to also connect the other end of the tube 11 in a similar manner to another artery or another arterial region without a suture having to be applied for the connection.

An inner lining, which is not shown in the drawing, can basically also be provided at the metal grid 13 instead of or in addition to the jacket 15. In this case, the inner lining would have to be provided with a suitable transmission orifice in the region of the connection point 21. Optionally, the metal grid 13 can also have a through-opening in the region of the orifice 17.

Both the jacket 15 and the tube 16 are provided with peripheral corrugation 16, whereby the required flexibility of the tube 11 and the combination of metal grid 13 and jacket 15 is increased.

The orifice 17 should be 0.8 to 1.8 cm long seen in the direction of the central axis 18.

The introduction of the prosthesis tube connection in accordance with the invention fixed on a balloon catheter in the folded state into the artery or aorta can also be carried out via an introducing tool, a so-called lock, with a maximum diameter of 12 mm, which is also known as vessel puncturing. The introducing tool is conically shaped and effects an expansion of the artery or main artery at the point of puncture.

In this way, a time-consuming preparation and a clamping off of the artery or aorta and the surgical opening of the vessel are dispensed with.

What is claimed is:

1. A tubular prosthesis for connecting two arterial regions inside a human body comprising a flexible, blood impermeable prosthesis tube having ends that can be introduced into the arterial regions for connection thereto in a blood-tight manner, a tubular, flexible, blood-tight jacket having a connecting orifice, the tube being directly connected to the jacket in a vicinity of the orifice in a blood-tight manner to establish flow communication between the orifice and an inner space of the tube, a folded, expandable tubular metal grid disposed inside and extending substantially over the entire length of the jacket and in its expanded state having substantially the same diameter as the arterial region, the jacket and the grid being arranged at an angle to a longitudinal axis of an end region of the tube in a vicinity of the orifice and having a length so that the jacket and the grid in its collapsed state can be introduced into the arterial region through an aperture in the arterial region and So that the jacket and the grid can be positioned to extend from the aperture in both directions along the artenal region, the jacket and the grid being dimensioned to engage the arterial region in a blood-tight manner when the grid inside the jacket is in its expanded state, a normally deflated balloon catheter disposed inside the metal grid to enable introduction of the metal grid and the surrounding jacket into the arterial region when the grid is in its folded state and the balloon catheter is deflated, means for inflating the balloon for expanding the metal grid and the jacket into blood-tight contact with the arterial region, a feed line in fluid communication with an interior of the balloon and extending laterally from a middle region of the balloon through the tube, and including a hand-operated valve adapted to be connected to a source of compressed air and fluidly coupled with the line for selectively opening the valve and thereby expanding the balloon and the surrounding metal grid.

2. A tubular prosthesis according to claim 1 wherein the jacket comprises one of polyethylenterephthalate and polytetra-fluoroethylene.

3. A tubular prosthesis according to claim 1 wherein at least one of the tube and the jacket includes a peripheral corrugation.

4. A tubular prosthesis according to claim 1 wherein the orifice in the jacket has an oval shape, a longer axis of the oval shape orifice extending in a longitudinal,direction of the jacket and the metal grid.

5. A tubular prosthesis according to claim 1 wherein a connection between the tube and one of the metal grid and the jacket is formed by one of suturing, weaving, welding and bonding.

6. A tubular prosthesis according to claim 1 wherein the metal grid in a vicinity of the orifice is closed and free of through openings.

7. A tubular prosthesis according to claim 1 wherein the metal grid has/an opening in a vicinity of the orifice corresponding to a diameter of the tube.

8. A tubular prosthesis according to claim 1 wherein blood flows through the first arterial region and past the aperture in a flow direction, wherein the metal grid has first and second sections lying upstream and downstream, respectively, of the orifice in the jacket, and wherein the first section of the jacket is longer than the second section of the jacket.

9. A tubular prosthesis according to claim 8 wherein the first metal grid section has a length in the range of 1.5 to 2 cm and the second section has a length of between 1 to 1.5 cm.

10. A tubular prosthesis according to claim 9 wherein the first section has a length of 1.7 cm and the second section has a length of 1.3 cm.

11. A tubular prosthesis according to claim 8 wherein the first metal grid section is between 10% to 30% longer than the second section.

12. A tubular prosthesis according to claim 11 a wherein the first section is approximately 20% longer than the second section.

13. A tubular prosthesis according to claim 1 wherein the orifice in the jacket has an axial length in a longitudinal direction of the jacket and the metal grid, and wherein a section of the jacket downstream of the orifice in the jacket is between 5% to 15% shorter than the axial length of the orifice.

14. A tubular prosthesis according to claim 1 wherein the tube has a diameter between 8 to 18 mm.

15. A tubular prosthesis according to claim 1 wherein the metal grid and the jacket have a length between 4.5 to 5.5 cm.

16. A tubular prosthesis according to claim 1 wherein at least one of the metal grid and the jacket have a diameter between 1.5 to 2.5 cm.

17. A tubular prosthesis according to claim 1 wherein the angle between the longitudinal axis of an associated end region of the tube and the jacket and the grid is between 30° to 60°.

18. A tubular prosthesis according to claim 17 wherein the angle is approximately 45°.

* * * * *